United States Patent
Nash

[19]

[11] Patent Number: 5,938,672
[45] Date of Patent: Aug. 17, 1999

[54] SYSTEM AND METHOD OF USE FOR REVASCULARIZING STENOTIC BYPASS GRAFTS AND OTHER BLOOD VESSELS

[75] Inventor: John E. Nash, Downingtown, Pa.

[73] Assignee: Kensey Nash Corporation, Exton, Pa.

[21] Appl. No.: 09/006,910

[22] Filed: Jan. 13, 1998

Related U.S. Application Data

[63] Continuation of application No. 08/900,598, Jul. 25, 1997, abandoned, which is a continuation-in-part of application No. 08/690,438, Jul. 26, 1996, Pat. No. 5,779,721.

[51] Int. Cl.[6] .................................................. A61B 17/22
[52] U.S. Cl. ............................................................ 606/159
[58] Field of Search .................................. 606/159, 170, 606/167, 180; 604/22

[56] References Cited

U.S. PATENT DOCUMENTS

| | | |
|---|---|---|
| 4,445,509 | 5/1984 | Auth . |
| 4,589,412 | 5/1986 | Kensey .................................... 606/159 |
| 4,631,052 | 12/1986 | Kensey . |
| 4,679,558 | 7/1987 | Kensey et al. . |
| 4,686,982 | 8/1987 | Nash . |
| 4,696,667 | 9/1987 | Masch . |
| 4,700,705 | 10/1987 | Kensey et al. . |
| 4,747,821 | 5/1988 | Kensey et al. . |
| 4,749,376 | 6/1988 | Kensey et al. . |
| 4,762,129 | 8/1988 | Bonzel . |
| 4,790,813 | 12/1988 | Kensey . |
| 4,842,579 | 6/1989 | Shiber . |

(List continued on next page.)

FOREIGN PATENT DOCUMENTS

| | | |
|---|---|---|
| 0 353 087 | 1/1990 | European Pat. Off. . |
| WO 93/00119 | 1/1993 | WIPO . |
| WO 95/21576 | 8/1995 | WIPO . |

OTHER PUBLICATIONS

Brochure entitled "Rotablator" by Heart Technology, Inc., Publication date unknown.
Brochure entitled "Extraction Atherectomy, Putting Plaque and Thrombus in Their Proper Place" by Interventional Technologies, Inc., Publication date unknown.
Publication by Possis Medical, Inc. Innovations for Life entitled AngioJet Rapid Thrombectomy System:, pp. 94 and 95, dated May, 1996.
Brochure entitled "Rheolytic Thrombectomy System Angio-Jet" by Possis Medical, Inc. Innovations for Life, Publication date unknown.
Brochure entitled "Amplatz Thrombectomy Device, The Clot–Buster" by Microvena Corporation, Publication date unknown.

*Primary Examiner*—Michael Buiz
*Assistant Examiner*—Kevin Truong
*Attorney, Agent, or Firm*—Caesar, Rivise, Bernstein, Cohen & Pokotilow, Ltd.

[57] ABSTRACT

A system and method for opening a lumen in an occluded blood vessel, e.g., a coronary bypass graft, of a living being. The system comprises an atherectomy catheter having a working head, e.g., a rotary impacting impeller, and a debris extraction sub-system. The atherectomy catheter is located within a guide catheter. The working head is arranged to operate on, e.g., impact, the occlusive material in the occluded vessel to open a lumen therein, whereupon some debris may be produced. The debris extraction sub-system introduces an infusate liquid at a first flow rate adjacent the working head and withdraws that liquid and some blood at a second and higher flow rate, through the guide catheter to create a differential flow adjacent the working head, whereupon the debris is withdrawn in the infusate liquid and blood for collection outside the being's body. The introduction of the infusate liquid may also be used to establish an unbalanced flow adjacent the working head to enable the atherectomy catheter to be steered hydrodynamically. A guide wire having an inflatable balloon on its distal end may be used with the atherectomy catheter to block the flow of debris distally, while enabling distal tissues to be perfused with an oxygenating liquid.

29 Claims, 6 Drawing Sheets

U.S. PATENT DOCUMENTS

| | | |
|---|---|---|
| 4,857,045 | 8/1989 | Rydell . |
| 4,883,458 | 11/1989 | Shiber . |
| 4,898,575 | 2/1990 | Fischell et al. . |
| 4,957,482 | 9/1990 | Shiber . |
| 5,002,553 | 3/1991 | Shiber . |
| 5,009,659 | 4/1991 | Hamlin et al. . |
| 5,030,201 | 7/1991 | Palestrant . |
| 5,042,984 | 8/1991 | Kensey et al. . |
| 5,047,040 | 9/1991 | Simpson et al. . |
| 5,074,841 | 12/1991 | Ademovic et al. . |
| 5,087,265 | 2/1992 | Summers . |
| 5,097,849 | 3/1992 | Kensey et al. . |
| 5,114,399 | 5/1992 | Kovalcheck . |
| 5,195,956 | 3/1993 | Stockmeier .............................. 606/159 |
| 5,224,945 | 7/1993 | Pannek, Jr. . |
| 5,267,955 | 12/1993 | Hanson . |
| 5,273,526 | 12/1993 | Dance et al. . |
| 5,282,484 | 2/1994 | Reger . |
| 5,284,486 | 2/1994 | Kotula et al. . |
| 5,314,407 | 5/1994 | Auth et al. . |
| 5,358,472 | 10/1994 | Vance et al. . |
| 5,366,463 | 11/1994 | Ryan . |
| 5,368,603 | 11/1994 | Halliburton . |
| 5,370,609 | 12/1994 | Drasler et al. . |
| 5,370,651 | 12/1994 | Summers . |
| 5,402,790 | 4/1995 | Jang et al. . |
| 5,409,454 | 4/1995 | Fischell et al. . |
| 5,423,742 | 6/1995 | Theron . |
| 5,429,136 | 7/1995 | Milo et al. . |
| 5,496,267 | 3/1996 | Drasler et al. . |

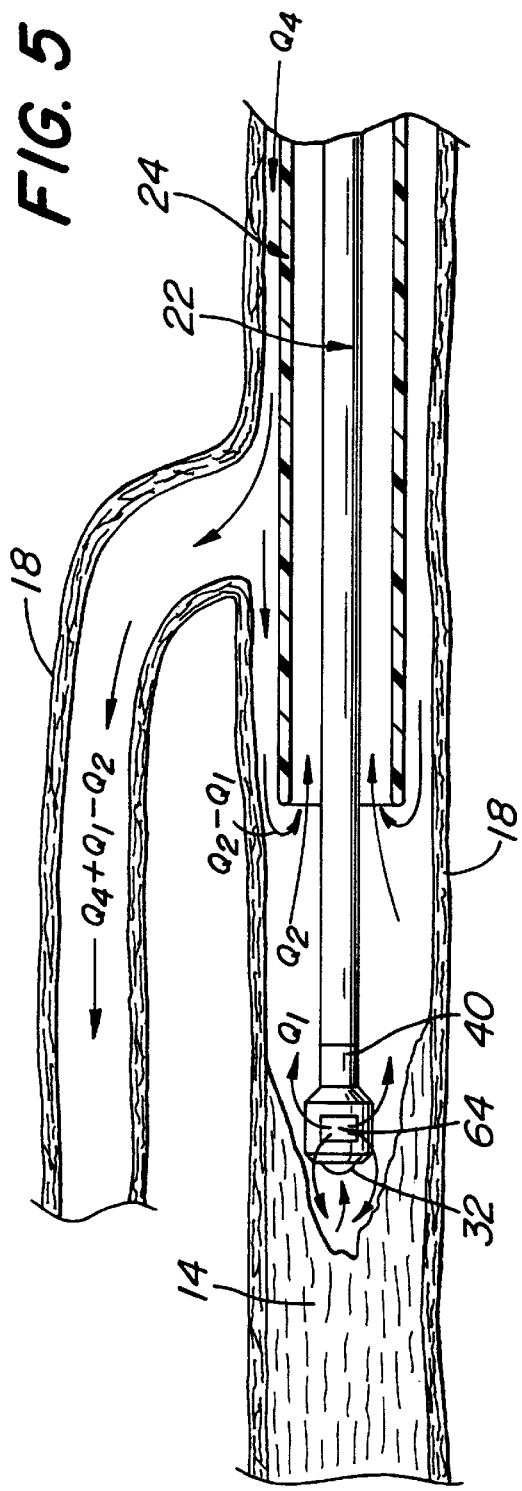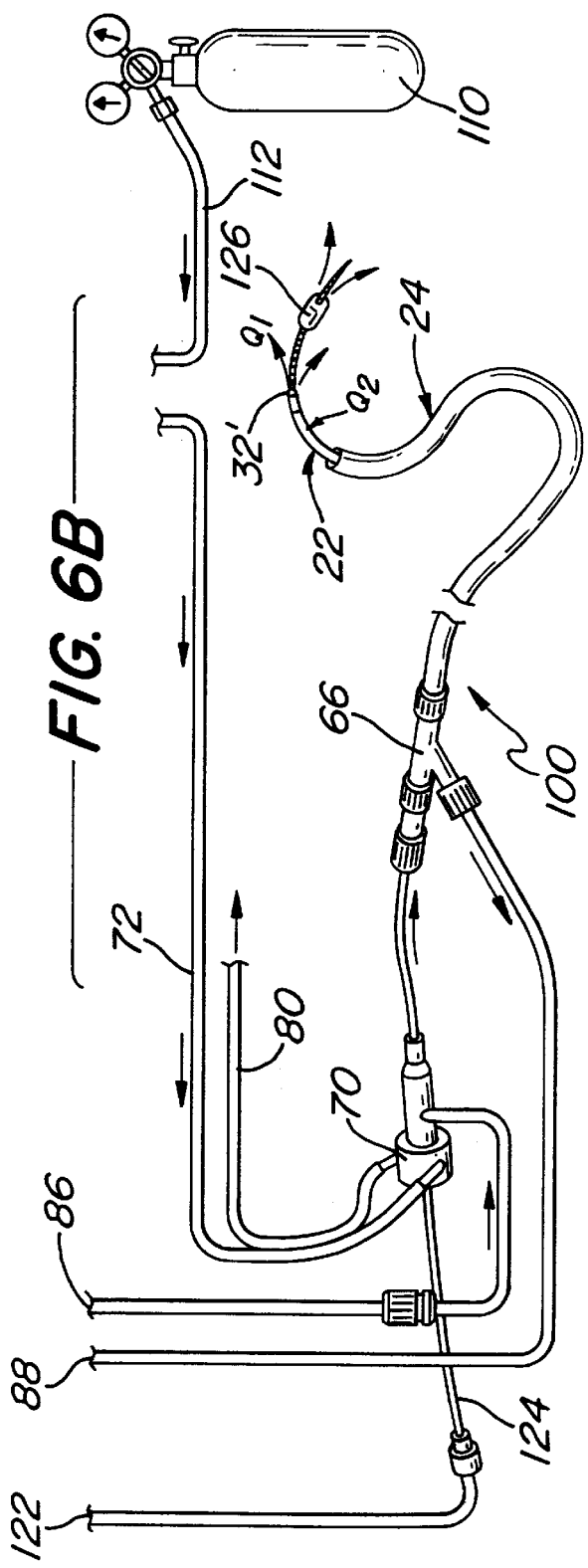

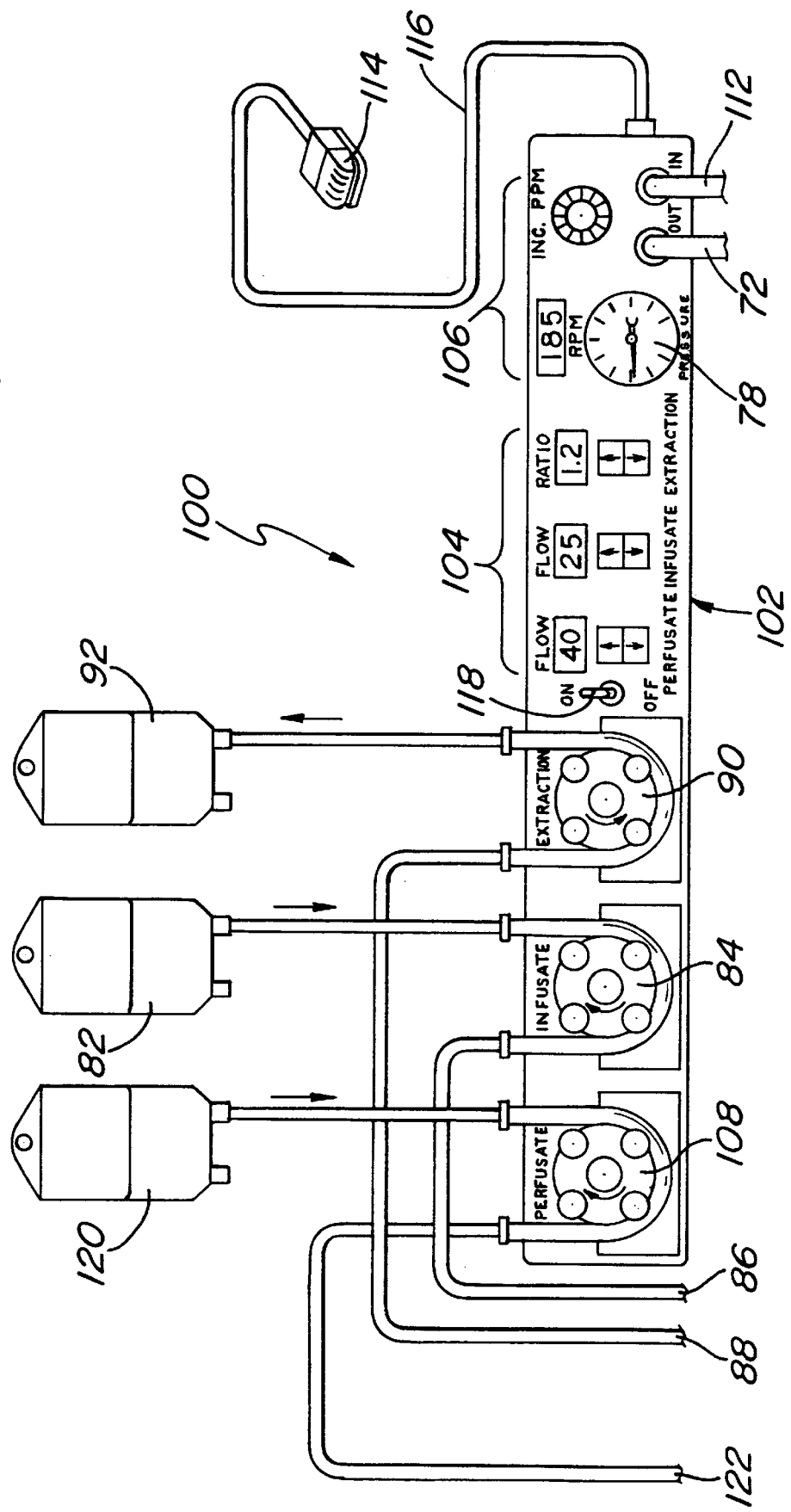

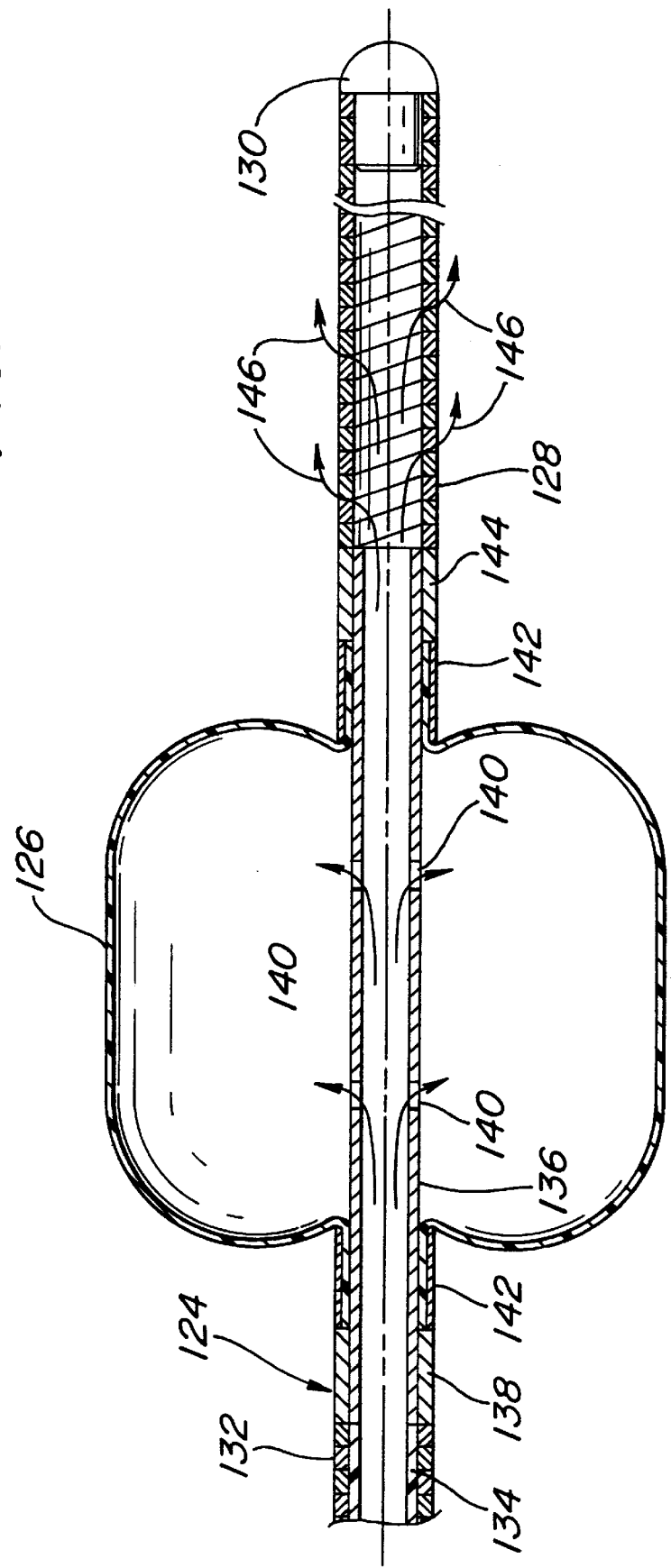

SYSTEM AND METHOD OF USE FOR REVASCULARIZING STENOTIC BYPASS GRAFTS AND OTHER BLOOD VESSELS

RELATED APPLICATION

This application is a Continuation of U.S. patent application Ser. No. 08/900,598, filed on Jul. 25, 1997, now abandoned, entitled System And Method Of Use For Revascularizing Stenotic Bypass Grafts And Other Blood Vessels, which in turn is a Continuation-In-Part of U.S. application Ser. No. 08/690,438, filed on Jul. 26, 1996, entitled System And Method Of Use For Revascularizing Stenotic Bypass Grafts And Other Blood Vessels now U.S. Pat. No. 5,779,721, both of which are assigned to the same assignee as this invention, and whose disclosures are incorporated by reference herein.

BACKGROUND OF THE INVENTION

This application relates generally to medical instruments and methods of use to remove occlusive material from a vessel, duct or lumen within the body of a living being.

Catheter instruments have been suggested or disclosed in the patent literature for effecting non-invasive or minimally invasive revascularization of occluded arteries. For example, in U.S. Pat. No. 4,445,509 there is disclosed a recanalization catheter designed specifically for cutting away hard, abnormal deposits, such as atherosclerotic plaque, from the inside of an artery, while supposedly preserving the soft arterial tissue. That recanalizing catheter includes a sharp-edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon relatively hard deposits are cut away from relatively soft tissue. Suction ports are provided to pull the hard particles produced by the cutting action into the catheter for removal at the proximal end thereof so that such particles do not flow distally of the catheter where they could have an adverse effect on the patients' body.

In U.S. Pat. No. 4,700,705, which is assigned to the same assignee as this invention and whose disclosure is incorporated by reference herein, there are disclosed and claimed catheters and methods of use for effecting the opening of a vessel, duct or lumen, such as the opening of a atherosclerotic restriction (partial or total occlusion) in an artery. These catheters are elongated flexible members of sufficient flexibility to enable them to be readily passed through the body of the patient to the situs of the atherosclerotic plaque in the artery to be opened. A working head is mounted at the distal end of the catheter and is arranged for high-speed rotation about the longitudinal axis of the catheter. In some embodiments the catheter may eject fluid at the working head to expedite the restriction-opening procedure.

In U.S. Pat. No. 4,747,821, which is also assigned to the same assignee as this invention and whose disclosure is incorporated by reference herein, there is disclosed and claimed other catheters particularly suited for revascularization of arteries. Each of those catheters includes a rotary working head having at least one non-sharp impacting surface to effect material removal without cutting. Moreover, those catheters are arranged to eject fluid adjacent the working head to expedite the revascularization procedure. In particular, the rotation of the working head produces a powerful, toroidal shaped vortex contiguous with the working head which has the effect of recirculating any particles that may have been broken off from the material forming the arterial restriction so that the working head repeatedly impacts those particles to reduce their size.

In U.S. Pat. No. 5,042,984, which is also assigned to the same assignee as this invention and whose disclosure is incorporated by reference herein, there are disclosed and claimed catheters whose working heads include impacting surfaces of differing aggressiveness which may be selectively brought into engagement with the restriction to be opened. Such catheters also make use of exiting jets of liquid as described above.

Other atherectomy devices for enlarging an opening in a blood vessel have been disclosed and claimed in the following U.S. Pat. No. 4,589,412 (which is assigned to the same assignee as this invention and whose disclosure is incorporated by reference herein); U.S. Pat. Nos. 4,631,052; 4,686,982 (which is assigned to the same assignee as this invention and whose disclosure is incorporated by reference herein); U.S. Pat. No. 4,749,376 (which is assigned to the same assignee as this invention and whose disclosure is incorporated by reference herein); U.S. Pat. Nos. 4,790,813; 5,009,659; 5,074,841; 5,282,484; 5,366,463; 5,368,603; 5,402,790; 5,423,742; and 5,429,136.

Some rotary atherectomy devices are in use in this country for revascularizing occluded arteries. However, their use is limited to some very selected applications. Thus, in many instances a vascular occlusion of a coronary artery can only be treated by coronary bypass surgery wherein a graft, e.g., a saphenous vein section and/or mammary artery section, is surgically shunted across the occluded coronary artery. Unfortunately a significant percentage of bypass surgical grafts become re-occluded over time. Thus, the re-occluded graft has to be either bypassed by another graft (i.e., second bypass surgery), or the re-occluded graft has to be revascularized (i.e., its lumen reopened) by some intravascular procedure. If the occluded graft is not totally occluded, balloon angioplasty may be indicated to reopen the graft. Where, however, the graft is totally occluded balloon angioplasty in unavailable. Thus, if revascularization of that graft is desired, resort may be to rotary atherectomy.

One currently available rotary atherectomy device is the ROTOBLACOR® System of Heart Technology, Inc. That system utilizes a catheter having a diamond coated elliptical burr which is rotated at a high rate of speed, e.g., up to 190,000 rpm. The burr serves to break the atherosclerotic plaque into fine particles which are allowed to remain in the patient's body for disposal by the patient's reticuloendothelial system.

As is known to those skilled in the art, one problem with a rotary atherectomy device is that unless the debris produced is so small and benign that it can be left within the patient's vascular system there must be some means to ensure that the debris does not flow upstream into the aorta during the procedure or into the downstream artery graft at the break-through point when the device comes out the distal side of a total occlusion, since either action could present a significant hazard to the patient. In particular, the former route risks stroke, the later route risks local ischemia of heart muscle when debris blocks off small arteries.

Thus, the collection and/or aspiration of debris produced during the revascularization of occluded arterial bypass grafts or other blood vessels is getting considerable attention in the medical arts. For example, Possis Medical, Inc., the assignee of U.S. Pat. Nos. 5,370,609 and 5,496,267, provides catheter devices designated as the ANGIOJET Rapid Thrombolectomy System and the ANGIOJET Rheolytic Thrombolectomy System. These devices are presumably constructed in accordance with those patents and are believed to be presently undergoing clinical trials. The catheter devices disclosed in those patents utilize high velocity jets of saline to abrade the blockage. In particular, the patents disclose utilizing the momentum of the saline jets to create a local vacuum to entrain any particulate material produced by the revascularization procedure, with the momentum and the local positive pressure being sufficient to carry the saline and debris to a return collection bag.

Another atherectomy device which is currently undergoing clinical trials is the Coronary TEC® System of Interventional Technologies, Inc. That device is believed to be the subject of U.S. Pat. No. 5,224,945, and basically comprises a catheter having a working head with microtome sharp blades for cutting plaque circumferentially. The excised plaque is extracted by suction through a central lumen in the catheter into an exteriorly-located vacuum bottle. No control of the quantity of flow of the debris-carrying fluid from the catheter is disclosed.

U.S. Pat. No. 5,030,201 (Palestran) discloses a system including an expandable atherectomy catheter arranged to be rotated to cut through an occluded artery to revascularize it. The atherectomy catheter includes an expandable cutting head having plural elongated cutting members which are mounted on a flexible torque tube incorporating a vacuum or aspiration system for retrieval of excised material. The cutting head is arranged to be rotated to cause the elongated members to cut away atheromatous material or blood clots. The atherectomy catheter is arranged to be inserted into the blood vessel through a coaxial delivery catheter, also forming a part of the system. The mechanism for aspirating particles of atheromatous material or blood clots removed by the elongated cutting members is disclosed as being in the form of a vacuum port provided at the proximal end of either the delivery catheter, the atherectomy catheter or a "retracting catheter" which also constitutes a part of the system. Saline solution or some other irrigant is infused through one of the catheters of the device that is not being used for aspiration. The infusion rate of the saline solution is balanced with the aspiration rate to avoid any net removal of fluid from the vessel. In particular, the patent teaches that by balancing the infusion rate of the saline solution to the aspiration rate, the net removal of fluid from the vessel can be brought close to zero, thereby minimizing blood loss.

While the balancing of the infusion and aspiration flow rates to minimize blood loss may be desirable, such action does not insure positive removal of all debris produced during the revascularization procedure.

Accordingly, a need exists for apparatus and a method of use to revascularize partially or totally occluded blood vessels, while positively assuring that any particles produced during the revascularization procedure are removed from the patient's body. In the case of partially or totally occluded coronary bypass grafts, a need exists for intravascular atherectomy apparatus and methods of use for effectively producing a lumen through the occlusion for the free flow of blood, without the risk that any debris produced during the lumen opening procedure will enter into the aorta or downstream of the occlusion once it has been crossed or opened.

OBJECTS OF THE INVENTION

Accordingly, it is a general object of this invention to provide systems and methods which address those needs.

It is another object of this invention to provide a system and methods for effectively revascularizing partially or totally occluded blood vessels and for removing any debris produced during the procedure from the patient's body.

It is another object of this invention to provide a system and methods for safely revascularizing partially or totally occluded blood vessels.

It is still another object of this invention to provide a system and methods for effectively opening a lumen in a partially or totally occluded arterial bypass graft, without the risk of debris produced during the procedure entering the aorta or from flowing downstream once the lumen through the occlusion has been opened.

It is yet another object of this invention to provide a system and methods for effectively opening a lumen in a partially or totally occluded portion of an artery, e.g., the femoral artery, downstream of a junction with another vessel, e.g., the profunda femoris, without the risk of debris produced during the procedure entering the other vessel or from flowing downstream in the artery once the lumen through the occlusion has been opened.

It is yet a further object of this invention to provide a system and methods for revascularizing partially or totally occluded blood vessels utilizing liquid infusion and aspiration means for establishing a differential flow to positively ensure the aspiration of debris produced during the revascularization procedure.

It is yet a further object of this invention to provide a system and methods for revascularizing partially or totally occluded blood vessels utilizing liquid infusion and aspiration means which is easy to operate to effect the positive removal of debris produced during the revascularization procedure.

It is yet a further object of this invention to provide a system and methods for revascularizing partially or totally occluded blood vessels utilizing liquid infusion and aspiration means which is adjustable for effectuating the positive removal of debris produced during the revascularization procedure.

SUMMARY OF THE INVENTION

These and other objects of this invention are achieved by providing a system for opening a lumen in an occluded blood vessel, e.g., a coronary bypass graft, of a living being's vascular system located downstream of another blood vessel, e.g., the aorta, from which blood will flow to the occluded blood vessel. The system basically comprises a working head for revascularizing the vessel and means for extracting or removing debris produced by operation of the working head.

The working head, e.g., a rotary impacting impeller, is arranged to operate on, e.g., engage, material, such as an atherosclerotic deposit or lesion or thrombus forming the occlusion within the interior of the occluded blood vessel to open a lumen for the flow of blood therethrough.

The debris extraction means is arranged to introduce an infusate liquid at a first flow rate into the vessel adjacent the working head and to withdraw that liquid and some blood at a second and higher flow rate from the vessel. This action creates a differential flow in the vessel, whereupon debris within the vessel which is produced by the action of the working head on the occlusion material is positively withdrawn with the infusate liquid and blood from the vessel for remote collection, e.g., in a collection vessel located outside the body of the person being treated. Thus, the differential flow serves to prevent the debris from flowing into adjacent blood vessels, e.g., the aorta.

In accordance with one preferred embodiment of this invention a debris blocking means, e.g., an inflatable balloon is provided at the distal end of the instrument. The debris blocking means is arranged to be operated, e.g., the balloon inflated, to physically block the egress of any debris downstream of the apparatus. Perfusion means is preferably provided to inflate the balloon and to oxygenate downstream tissue when the balloon is inflated.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 5, is an illustration showing the apparatus of FIG. 1, partially in section, during the process of revascularizing a totally occluded femoral artery downstream of the profunda femoris;

FIGS. 6A and 6B together are an illustration of another embodiment of the system of this invention for revascularizing or opening a lumen in a coronary bypass graft;

FIG. 8 is an enlarged longitudinal sectional view of the distal end of the instrument shown in FIG. 7.

DETAILED DESCRIPTION OF THE PREFERRED EMBODIMENT

Figure 1:
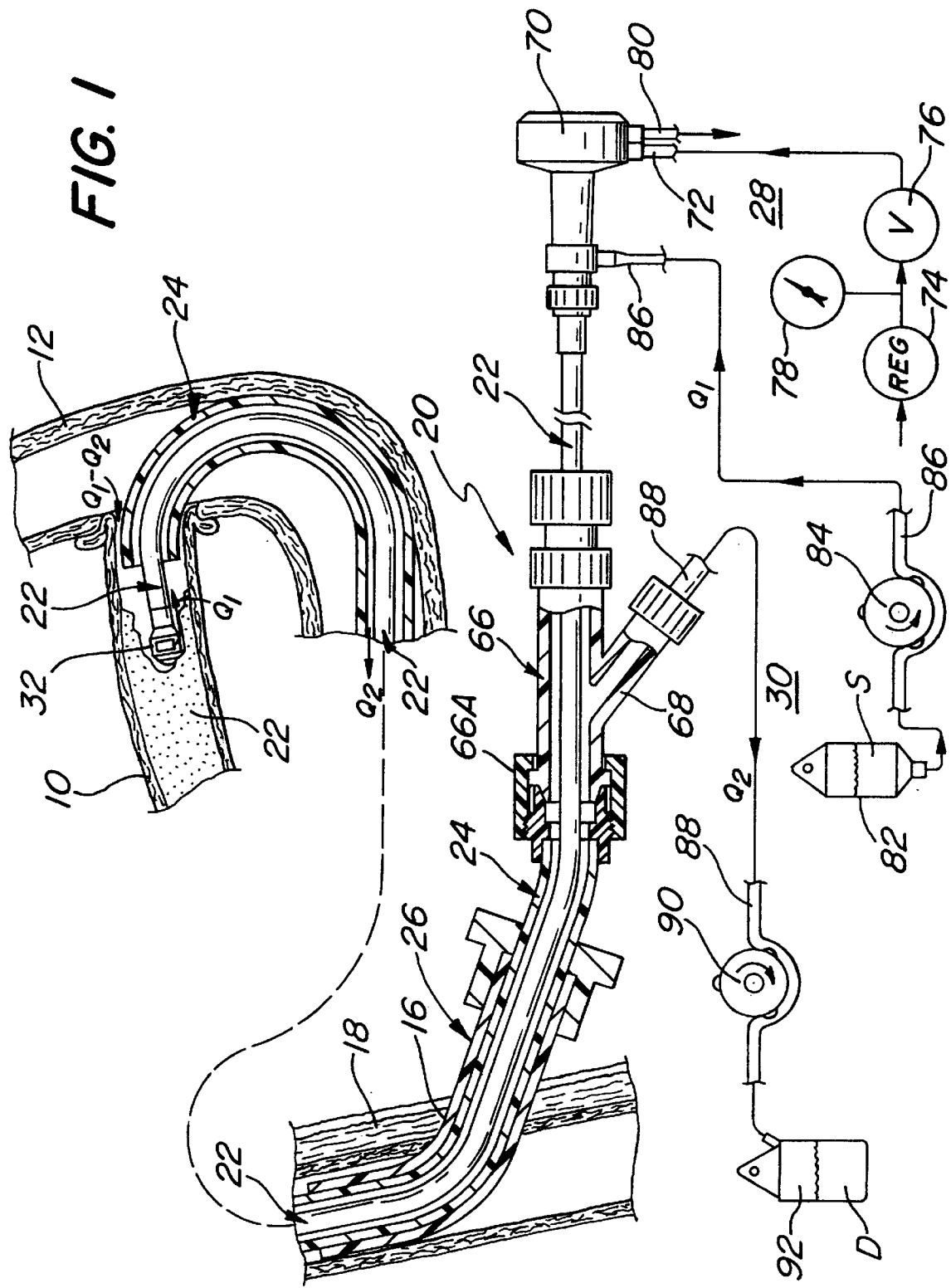
FIG. 1 is a schematic diagram, partially in section, of a system of the subject invention shown during the process of opening a lumen in a totally occluded coronary bypass graft so that blood can flow therethrough.
Figure 2:
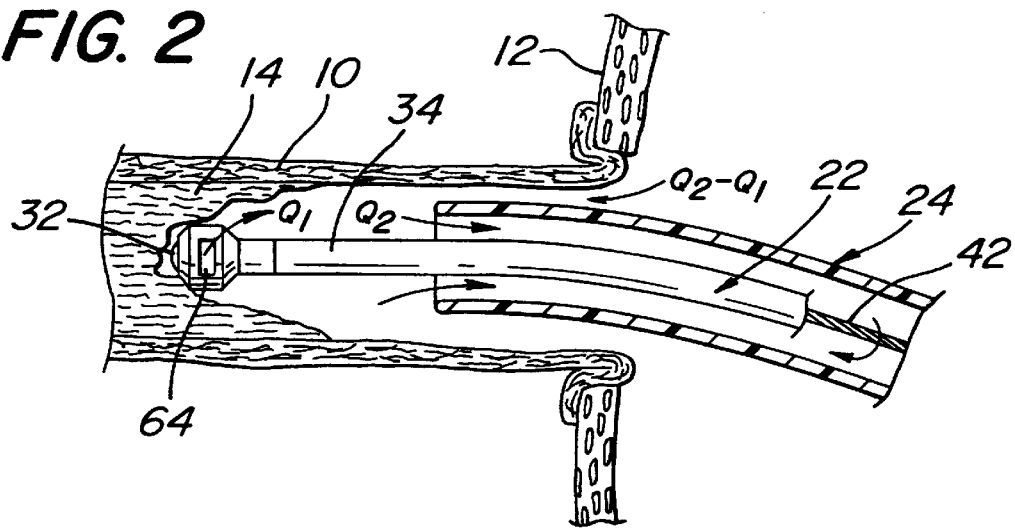
FIG. 2 is an enlarged view, partially in section, of a portion of the system of FIG. 1 shown during the process of opening a lumen in the occluded coronary bypass graft.

Referring now in greater detail to the various figures of the drawings wherein like reference characters refer to like parts, there is shown at 20 in FIG. 1 a system for revascularizing or opening a lumen through a coronary bypass graft which has become occluded, such as by the formation of a stenotic lesion or the build-up of plaque therein. As used herein the term "occluded" is given its broadest interpretation. Thus, an "occluded" graft or blood vessel may be either totally blocked or only partially blocked (i.e., there is a passageway or lumen through which some blood may flow).

The system 20 is arranged to be used for forming or enlarging a lumen through any blood vessel within the body of a living being, e.g., an occluded femoral artery downstream of the profunda femoris, not necessarily an occluded coronary bypass graft or an occluded coronary artery. In particular, the system 20 is arranged to produce a channel or lumen or to enlarge a lumen through the occlusive material within the vessel and to ensure that any particles of that material which are removed or broken away, during the revascularization procedure are prevented from flowing into the contiguous vascular system. When the system 20 is used for revascularization of occluded coronary bypass grafts, a primary application for the system 20, the debris produced is drawn into the system for extracorporeal removal and is thus prevented from entering the aorta.

As can be seen in FIG. 1, the system 20 basically comprises an "atherectomy" catheter 22, a guide catheter 24, an introducer sheath 26, a drive sub-system 28, and a debris removal sub-system 30. The atherectomy catheter 22 is in the form of an elongated flexible tubular body member or jacket at the free or distal end of which is located a rotatable working head 32. The working head 32 is generally similar to that described in U.S. Pat. No. 4,747,821. Alternatively, the working head may be constructed in accordance with the teachings of U.S. Pat. Nos. 4,679,558, 4,686,982, 4,749,376, 5,042,984, and 5,097,849, all of which are also assigned to the same assignee as this invention, and whose disclosures are also incorporated by reference herein. In fact, the working head may be any device for opening a lumen through the occlusive material.

In use the atherectomy catheter 22 is guided through the vascular system of the patient by the guide catheter 24 (which is conventionally placed) to the site of the vascular occlusion that has been determined to exist, so that the rotary working head is located immediately adjacent the upstream end of the occlusion. In the embodiment shown in FIG. 1, the atherectomy catheter is located within a coronary bypass graft 10 having an upstream end in fluid communication with the aorta 12. The downstream end of the graft is not shown and is in fluid communication with the coronary artery being bypassed or with smaller arteries of the heart. In the example shown herein the graft 10 is totally occluded by an atherosclerotic lesion or plaque or some other occlusive material 14 within the interior of the graft.

The atherectomy catheter 22 is introduced into the patient's vascular system in a conventional manner, e.g., via the use of the introducer sheath and guide catheter. As shown, this is accomplished via a percutaneous puncture 16 in the femoral artery 18. The sheath 26 and guide catheter 24 are each of conventional construction and thus their details will not be described in the interest of brevity.

The working head 32 is arranged to rotate about the longitudinal axis of the catheter at a high rate of speed, e.g., from 10,000 rpm to 200,000 rpm to repeatedly mechanically impact the occlusive material. At the same time, an infusate liquid (to be described later) is pumped through the atherectomy catheter by a pump (to be described later and forming a portion of the debris removal sub-system 30) and out of distal end of the atherectomy catheter adjacent the working head.

The opening of the occlusion to allow freer flow of blood therethrough is effected by impacting surfaces of the rotating working head impacting the occlusive material 14, whereupon portions thereof are removed, e.g., broken away. In addition, as will be described later, the rotation of the working head produces a powerful, toroidal shaped vortex contiguous with the working head. This vortex flow has the effect of recirculating any particles that are broken off from the occlusive material by the impact of the rotary working head's impacting surfaces back into contact with such surfaces. Accordingly, those particles are repeatedly impacted over and over, with each impaction reducing the size of the particles further until the resulting particle size is very small, e.g., 95% have a surface area less than that of a red-blood cell. At the same time another pump (also to be described later) of the debris removal sub-system 30 is operated to aspirate the particles produced during the revascularization procedure along with the infusate liquid and some blood.

Thus, as will be described in detail later, the debris removal subsystem 30 is operative to ensure that debris produced as the working head opens a lumen through the occlusion is not able to flow upstream into the upstream vessel, e.g., the aorta 12, during the lumen opening procedure, and once the working head breaks through or exits the occlusion on the downstream side, that the debris is not able to flow downstream into the downstream blood vessel(s).

Figure 4:
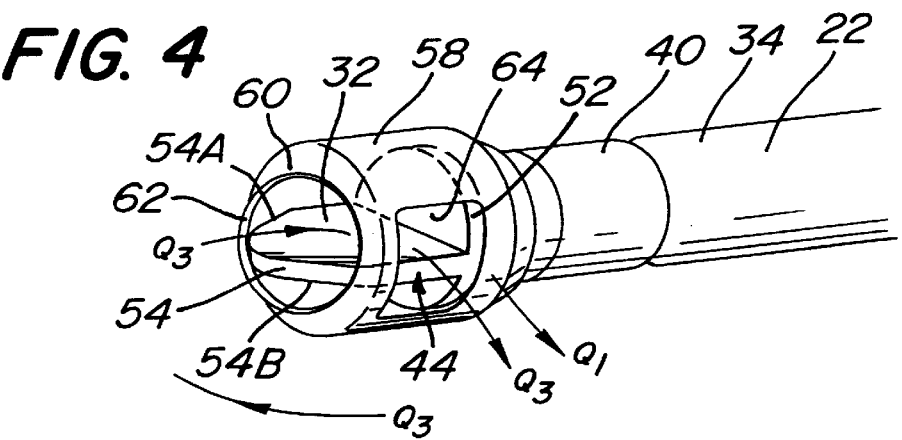
FIG. 4 is a reduced isometric view of the portion of the system shown in FIG. 3.

As best seen in FIG. 4 the atherectomy catheter includes a jacket 34 which is formed of any suitable material, e.g., plastic, and has a small outside diameter. In the preferred embodiment shown herein, the outside diameter of the jacket 34 is approximately 1.5 mm (5 French). This size catheter is merely exemplary. The means for effecting the rotation of the working head is the heretofore identified drive sub-system 28. That sub-system is similar to the drives disclosed in the aforementioned U.S. Pat. Nos. 4,686,982, and 4,747,821 and basically comprises an air-turbine motor and associated rotary drive cable (to be described later). Other drive systems can be utilized, as well.

Irrespective of the construction of the drive system, it is coupled to the working head 32 so that the working head is rotated about its longitudinal axis at the high rate of speed. Many of the details of the working head will be described later. Suffice it for now to say that the working head 32 includes an impeller portion 44 and a central shank portion or axle 36 (FIG. 4) projecting proximally therefrom. The axle 36 is supported in a central bore of a bushing 38 fixedly mounted at the distal end of the catheter's jacket 34 by an encircling mounting band 40. The shank 36 is fixedly secured to the distal end of a flexible drive cable 42 forming a portion of the drive sub-system 28.

The impeller 44 forms the distal portion of the working head and is fixedly secured to the shank 36 so that it will be rotated at a high rate of speed about its longitudinal axis by the concomitant rotation of the drive cable. The impeller portion 44 comprises a circular disk or base 52 from which a generally planar tip 54 projects. The tip 54 has a pair of generally planar diametrically disposed relieved side surfaces or faces which merge with an arcuate front or distal surface to form a pair of arcuate impacting surfaces 54A and 54B. Each of the impacting surfaces is radiused in a plane perpendicular to the axis of rotation of the working head so that each is not sharp, e.g., is in the range of approximately 0.001 inch to approximately 0.008 inch, although in the scale of the figures of the drawing they appear to be a sharp line. The working head is located within a cylindrical shroud 56 (FIGS. 3 and 4) fixedly mounted on the front of the bushing 38. The shroud 56 includes a cylindrical sidewall portion 58 and a generally conical distal wall portion 60 terminating in a circular opening 62 in the distal end thereof. The shroud may be of any suitable outside diameter, e.g., 7 to 8 French. The distal arcuate portion of the impeller tip 54 projects out of the central or front opening 62. A side port or open window 64 is located in the sidewall 58.

As mentioned earlier the system 20 utilizes an infusate liquid to expedite the revascularization of the vessel. In particular, the infusate liquid is pumped at a flow rate $Q_1$ (to be described later) down through the interior of the catheter jacket 34 through four equidistantly spaced grooves 46 extending down the central bore of the bushing 38 and via radial ports 48 to an annular recess 50 in the front wall of the bushing. The annular recess is in fluid communication with the side port or window 64 in the shroud so that the infusate liquid can exit therefrom. The direction of flow of the infusate liquid down the atherectomy catheter and out the shroud at its working head is shown clearly in FIG. 4.

Figure 3:
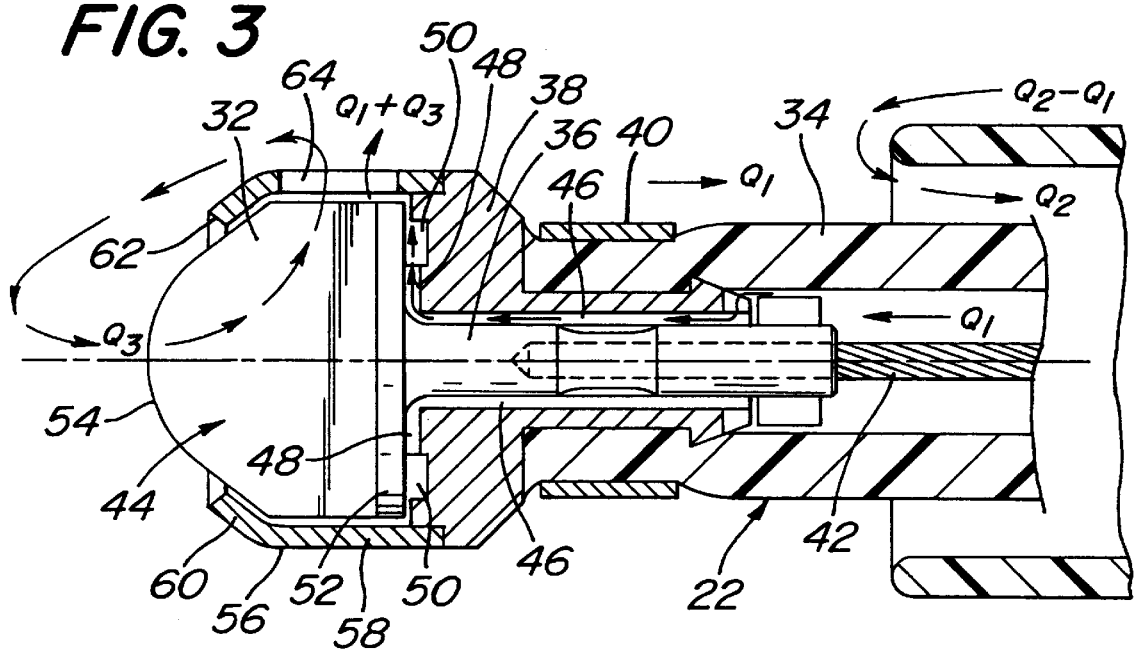
FIG. 3 is an even more greatly enlarged view, partially in section, of a portion of the system shown in FIG. 2.

The rotation of the working head about its longitudinal axis produces a powerful toroidal shaped vortex flow $Q_3$ in the fluid contiguous with the working head. This flow $Q_3$ circulates by entering into the shroud through the central or front opening 62 and exits out through the side window 64 as shown in FIG. 3. Thus, the flow exiting through window 64 is $Q_1+Q_3$. As will be appreciated by those skilled in the art the vortex flow $Q_3$ has the effect of recirculating any particles that are broken off from the occlusive material 14 by the action of the rotating working head back into contact with the working head's impacting surfaces. Thus, the occlusive material particles which are broken away are progressively reduced in size until they are aspirated by aspiration means forming a portion of the debris removal sub-system 30. That means will be described later. Suffice it for now to state that the aspiration means withdraws the infusate liquid, the debris particles and some blood at an aspiration flow rate of $Q_2$.

As should be appreciated by those skilled in the art the liquid exiting from the window 64 of the shroud will tend to push the atherectomy catheter's distal end sideways or laterally in the direction opposite to the direction of the liquid exiting that window. This hydrodynamic action can be effectively used to steer the catheter to a desired position with respect to an occlusion to be revascularized. In this regard, for example, when negotiating a branch in the artery system to reach the occlusion to be revascularized, the atherectomy catheter can be rotated or twisted about its longitudinal axis so that the shroud's window is facing in the opposite direction to the branch to be entered. This action will cause the side directed liquid exiting the window 64 to push the catheter's distal end sideways, whereupon it can enter the desired arterial branch. Such "hydrodynamic steering" of the atherectomy catheter can be accomplished in other manners and by other means than by the use of a shroud having a single side window or port. Thus, this invention contemplates an intravascular catheter instrument, of any type, including any means for producing an asymmetric, e.g., side directed, fluid flow adjacent the distal end of the catheter so that it can be steered into a desired position by appropriate rotation of the catheter about its longitudinal axis.

As mentioned earlier, the guide catheter 24 is of any conventional construction. In the preferred embodiment shown in FIG. 1 it is a 10 F to 12 F catheter having a conventional Y connector 66 at its proximal end. The Y connector 66 has one input leg including a Touhy-Borst adjustable hemostasis valve 66A through which the atherectomy catheter 22 passes. The other input leg, i.e., the angled leg 68, is connected to the aspiration portion of the debris removal sub-system 30 (to be described later).

Power for operating the atherectomy catheter is provided by the drive sub-system 28. That system includes an air turbine motor 70 which is coupled to the proximal end of the flexible drive cable 42. The air turbine 70 is provided with compressed air via an input line or conduit 72. Air for the line 72 is provided from a source (not shown) via an associated regulator 74, and the conventional control valve 76. The control valve is coupled to the input line 72 of the air turbine. A pressure gauge 78 is connected between the regulator 74 and the control valve 76. The regulator 74, the control valve 76, the pressure gauge 78 and the associated lines or conduits and the air source make up the drive sub-system 28. The control valve 76 is of any conventional construction, be it mechanical or electrical. The air turbine motor 70 is also of any conventional construction, as is the regulator 74 and the pressure gauge 78. The air turbine includes an outlet port in communication with the ambient atmosphere, via a line 80. It must be pointed out at this juncture that the atherectomy catheter 22 need not utilize an air turbine motor to rotate the working head. For example, an electric motor can be provided to replace the air turbine to drive the rotating cable and the associated working head.

The debris removal sub-system 30 basically comprises a source 82 of the infusate liquid "S", e.g., saline plus a 30% contrast media, a first positive displacement pump 84, an input line or conduit 86, an outlet line or conduit 88, a second positive displacement pump 90, and a debris collection vessel 92. The input line 86 and its associated components, i.e., the pump 84 and infusate source 82 serve as the "infusion" means for the system 20. To that end the input line 86 is coupled via a connector to the interior of the atherectomy catheter, i.e., to the annular space within the catheter's jacket between it and the drive cable. The infusate liquid S is pumped at the flow rate $Q_1$ by the positive displacement pump 84 through line 86 from the supply or source 82. Thus, the infusate liquid S exits the catheter's working head and circulates as described earlier.

The rate of flow $Q_1$ of the infusate liquid is established by the positive displacement pump 84 under control of some automatic or manual controller (not shown). In accordance with one exemplary method of use the pump is operated to produce a flow rate $Q_1$ the range of 5–80 ml. per minute.

The output line 88 and its associated components, i.e., the pump 90 and debris collector vessel 92 serve as the "aspirating" means for the debris removal sub-system 30. To that end, the aspiration line 88 is connected to the leg 68 of the Y connector 66. The pump 90 is arranged to be operated to pump the infusate liquid, the debris produced by the revascularization, and some small amount of blood at the flow rate $Q_2$ in the proximal direction through the annular space between the atherectomy catheter 22 and the guide catheter 24 and out through the connector leg 68 into the outlet line 88, and from there to the collector vessel 92.

The flow rate $Q_2$ is selected to be greater than $Q_1$ For example, in one exemplary method of use the flow rate is selected to be in the range of 5–100 ml. per minute, with the differential between $Q_2$ and $Q_1$ being between 5 and 50 percent. The use of an aspiration flow rate $Q_2$ which is higher than the infusion flow rate $Q_1$ insures that any debris, e.g., particles of the occlusive material making up the graft's lesion, produced from debriding that material is positively prevented from flowing into adjacent vessel portions. In this regard, as will be appreciated by those skilled in the art, since the aspiration flow rate $Q_2$ is greater than the infusion flow rate $Q_1$, some blood equal to $Q_2-Q_1$ will also be withdrawn from the upstream vessel, e.g., the aorta as shown in FIGS. 1 and 3. The withdrawal of some blood from that vessel insures that the debris produced cannot flow upstream to enter into it. Instead the debris particles will be entrained within the infusate liquid and blood which is withdrawn through the aspiration line. The rate of blood withdrawn is preferably be kept to a minimum, e.g., 40 ml. per minute in the interests of patient safety.

In accordance with a preferred aspect of this invention the operation of the pumps 84 and 90 are coordinated so that $Q_2$ is equal to some variable times $Q_1$, where that variable is greater than 1 and is adjustable to accommodate the needs of the patient. Moreover, the coordination of the flow rates is preferably accomplished automatically, so that a change in one flow rate automatically results in a proportional change in the other flow rate. This coordinated action may be accomplished by a mechanical linkage between the pumps, or by a common electrical controller for the pumps. Manual control of the pumps is also envisioned for some applications.

In any case, any suitable positive displacement pumps can be utilized, e.g., peristaltic pumps or piston pumps, in the system.

In order to expedite the revascularization of the bypass graft, the infusate liquid may be provided with a contrast medium, e.g., 30% contrast medium, so that the revascularization procedure can be viewed using conventional imaging techniques. Moreover, the infusate liquid can, if desired, be oxygenated to eliminate distal ischemia when the catheter is used for arterial restriction opening procedures. Also, if desired, small amounts of heparin, urokinase, etc., or other drugs can be added to the infusate liquid for the procedure.

As should be appreciated from the foregoing the subject invention provides a viable means for effecting the revascularization of partially or totally occluded coronary bypass grafts, while positively assuring that any debris particles produced during the revascularization procedure is removed from the patient's body. In addition, the subject invention is suitable for revascularizing other occluded vessels, as well. For example, in FIG. 5 the system is shown in use revascularizing a totally occluded femoral artery 18 downstream of the profunda femoris 18A. In this application the system functions to capture the debris created during the lumen opening procedure by preventing it from going along side the catheter and exiting down the profunda to end up in the distal capillary beds. In this application, a portion $Q_4+Q_1-Q_2$ of the blood flowing down the femoral artery 18 to the situs of the occlusion will be permitted to flow into the profunda femoris, while the portion $Q_2-Q_1$ of the blood and infusate liquid is diverted and/or withdrawn into the guide catheter to ensure positive debris removal in the same manner as described earlier. For some persons, e.g., diabetics with severely compromised distal capillary beds, a femoral artery revascularization procedure is likely to prove beneficial.

Turning now to FIGS. 6A and 6B, an alternative embodiment 100 of the system of the subject invention is shown. The system 100 is similar in most respects to system 20 described heretofore. One major difference, however, is that the atherectomy catheter is arranged for use over a guide wire (to be described later). The guide wire includes a debris blocking member, e.g., an inflatable balloon (also to be described later). When the atherectomy catheter is in place on the guide wire the balloon is located distally of the working head of the atherectomy catheter and the balloon serves to physically block any debris produced by the system 100 which may tend to escape extraction from flowing distally. The atherectomy catheter used in the system 100 is designated by the reference numeral 22' and is identical in most respects to the catheter 22 described heretofore. In the interests of brevity, the features common to catheters 22 and 22' will not be reiterated. So too, the features common to systems 100 and 20 will also not be reiterated. Moreover, in the interests of drawing simplicity common components will be given the same reference numerals.

As can be seen in FIGS. 6A and 6B, the system 100 includes a controller or console 102 housing the heretofore identified infusate pump 84 and the extraction pump 90. Each of these pumps is a peristaltic pump. The console 102 also includes a flow control section 104 for establishing the various fluid flows of the system, as will be described later, and a speed control section 106 for establishing the operational speed of the working head of the atherectomy catheter. The details of the speed control section 106 will also be described later. A perfusate pump 108 is also provided in the console 102. The perfusate pump 108 is also a peristaltic pump and its operation will be described later. Suffice it for now to state that the pump 108 is arranged to provide a perfusion liquid, e.g., blood or a suitable synthetic oxygenation liquid, downstream of the inflatable balloon to perfuse downstream (distally) located tissue. The pump 108 also serves to effect the inflation of the balloon.

Compressed gas (e.g., air or nitrogen) is provided via line 72 from the console 102 to the catheter's turbine 70. The console, in turn, receives the compressed gas from a tank 110 via an input line 112. The rotational speed of the turbine is controlled by the speed control section 106 of the console 102. On/off operation of the turbine is controlled by a turbine foot control pedal 114 and an associated gas line 116 connected to the console. This pedal also initiates operation of the infusate pump 84.

The speed control section 106 of the console includes a rotary knob for establishing the desired rotational speed of the turbine and an associated digital display for displaying the turbine's speed. The console also includes an on/off switch 118 for enabling electrical power to be provided to the system's electrical components when the switch is in the "on" position.

The foot pedal 114 is used by the operator of the system 100 to initiate operation of the infusate pump to cause the infusation liquid to flow down the guide wire and out its distal end and to start the atherectomy catheter's turbine 70 a short time, e.g., 2 seconds, after the infusate liquid begins to flow. The use of the foot pedal frees the operator's hands for other purposes.

The perfusate pump 108 is connected via an input line to a bag 120 containing the perfusion liquid. The output of the perfusate pump 108 is provided via a line 122 to the guide wire of the system 100. The guide wire is designated by the reference numeral 124 and includes the heretofore identified balloon. That balloon is designated by the reference number 126 and, as seen clearly in FIGS. 6B, 7 and 8, is located adjacent the distal end of the guide wire 124.

The atherectomy catheter 22' is an "over-the-wire" type of device. Thus, it includes a central lumen for receipt of the guide wire 124 so that the catheter 22' can be threaded over the guide wire 124. The guide wire 124 serves to perfuse distally located tissue and to inflate its balloon 126 so that the balloon blocks any particulate material (debris) from flowing distally. To accomplish these functions, the perfusate liquid in the bag 120 is pumped by the perfusate pump 108 through the line 122 and through the interior of the guide catheter 124 where some of it fills or inflates the balloon and the remainder exits at the distal end of the catheter to perfuse downstream tissue, as will be described later.

The rate of flow of the infusate, extraction and perfusate liquids is established by the flow control section 104 of the console via its various up/down switches and associated digital displays. As discussed earlier, the ratio of the infusate flow rate to the extraction flow rate is adjustable. This is accomplished by the appropriate setting of the "infusate flow" and "ratio" up/down switches of the flow control section of the console. The desired ratio and the infusate flow rate are displayed by the associated digital displays.

Figure 7:
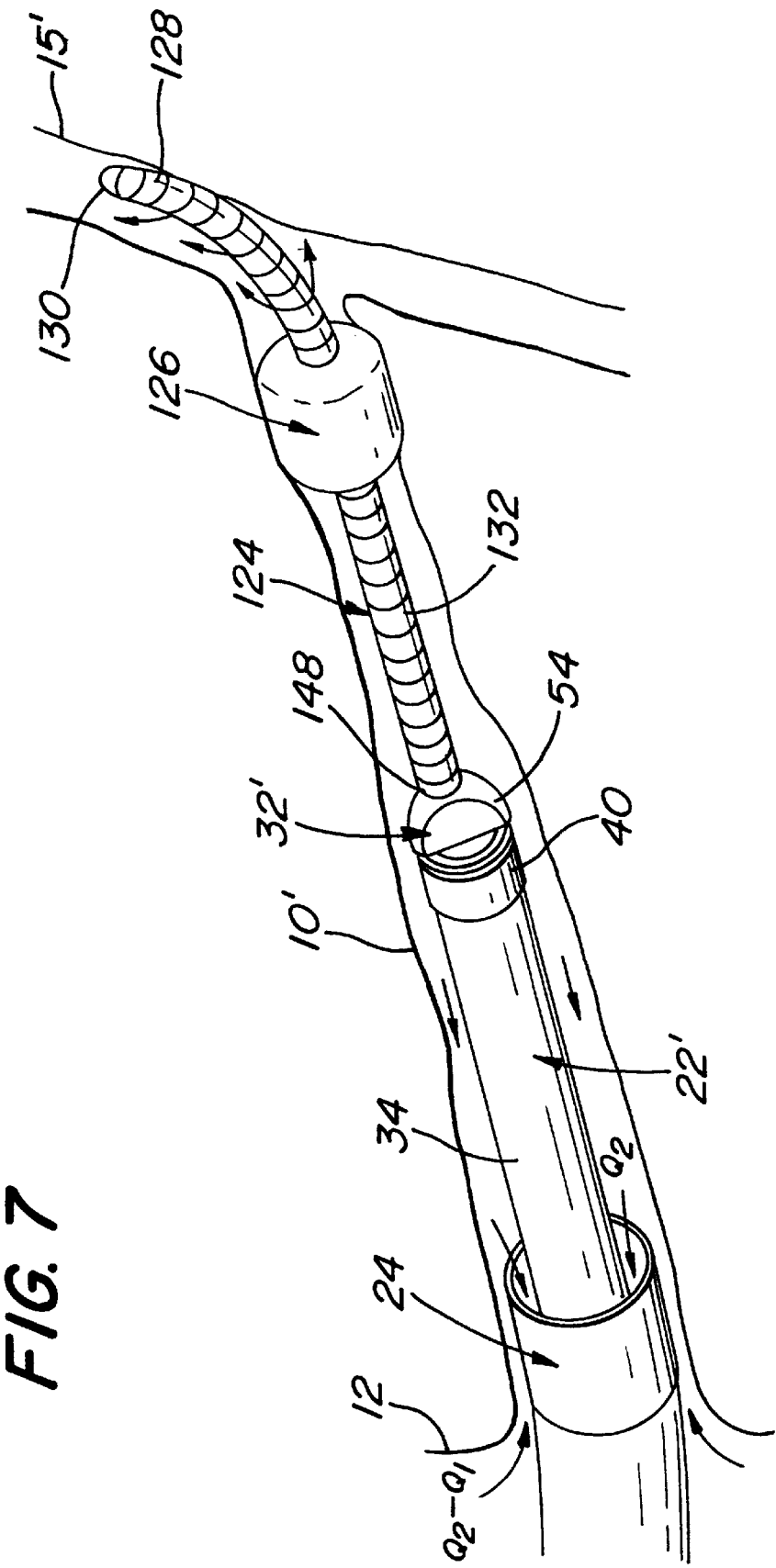
FIG. 7 is an enlarged isometric illustration of a portion of an instrument forming a component of the system shown in FIGS. 6A and 6B during the process of revascularizing a diseased bypass graft.

In FIG. 7 there is shown in greater detail the distal end of the atherectomy catheter 22' located within a diseased bypass graft, e.g., a re-occluded mammary artery 10'. The diseased artery leads to a distal blood vessel 15, i.e., the vessel to be fed by the graft 10'. The guide wire 124 is in the form of an elongated flexible member, whose construction will be described later with reference to FIG. 8. The distal end of the guide wire 124 is in the form of a somewhat soft or flexible, precurved tip 128. The free end of the catheter's tip is a hemispherical dome 130. The balloon 126 is disposed slightly proximally of the free end 130 of the guide wire 124.

In FIG. 8 the details of the distal end of the guide wire 124 and balloon are shown (although the tip 128 is shown being linear in the interest of drawing simplicity). Most of the length of the guide wire, i.e, from its proximal end to the location of the balloon 126, is in the form of a two start helical spring 132 (see FIG. 8) whose convolutions are in close engagement (abutment) with one another. The spring 132 enables the guide wire to be bent through a small radius of curvature to facilitate its intravascular placement via the conventional guide catheter 24. Inside the helical spring 132 is a liquid impervious, e.g., rubber or plastic, flexible liner tube 134. This tube prevents the egress of the perfusate liquid through the interface between successive convolutions of the helical spring 132 as that liquid is pumped down the guide wire 124.

A perforated support tube 136 is mounted within a distal end helix termination 138 of the spring 132. The support tube 136 is arranged to mount the balloon 126 thereon and includes a plurality of radially located apertures or ports 140. The balloon 136 is an annular member of any conventional construction, e.g., rubber, and is mounted on and is disposed about opposite ends of the perforated support tube 136. In particular, the balloon 136 is held in place and sealed to the periphery of the support tube at each end thereof via respective bands 142. Each band 142 extends about one cylindrical end of the balloon. Thus, when the perfusion liquid is pumped down the guide wire 124 by the pump 108 it passes through the apertures or ports 140 (as shown by the arrows in FIG. 8) to fill up, i.e., inflate, the balloon 126.

The distal end of the perforated support tube is located within a spring helix termination 144 forming the proximal end of the guide wire tip portion 128. The portion 128 is also formed as a two start helix, like portion 132. However, no fluid-impervious sleeve is located within the tip portion 128 so that the interface between successive convolutions of the spring forming the tip portion 128 serve as passageways through which the portion of the perfusion liquid which doesn't enter the balloon exits the guide wire as shown by the arrows 146 in FIG. 8.

Since the atherectomy catheter 22' is designed for over-the-wire use, the drive cable for rotating its working head is in the form of a spiral spring helix having a central lumen extending down its center. The proximal end of the drive cable is connected to the output of the turbine 70 while the distal end is connected to the working head. That working head is designated by the reference number 32' and is shown in FIGS. 6A and 7. The central lumen of the spiral helix drive cable forms the passageway for receipt of the guide wire 124. If desired an anti-friction sleeve or some other anti-friction bearing can be provided at the interface between the inner surface of the spiral drive cable and the outer surface of the guide wire. The working head 32' is similar in construction to the working head 32 of system 20 except that the working head 32' includes a central bore 148 through which the guide wire 124 extends. As can be seen clearly in FIG. 7, the working head 32' is unshrouded, i.e., is not located within a shroud like the working head 32 of the atherectomy catheter 22.

Operation of the system 100 is as follows:

The guide wire 124 with its balloon 126 deflated and with the atherectomy catheter 22' mounted thereon so that the balloon 126 and tip portion 128 extend beyond the working head 32' is threaded through a preplaced guide catheter 24 in the patient's vascular system until it is at a desired situs, such as at the arch of the aorta. At this point the guide wire 124 is advanced with respect to the atherectomy catheter 22' so that the guide catheter crosses the lesion or atherosclerotic deposits in the bypass graft 10'. The precurved tip of the guide wire 124 facilitates the placement of the guide wire. In this regard, the guide wire can be rotated about its longitudinal axis to point the tip 130 in the desired direction.

Once the guide wire 124 is at the desired position, such as shown in FIG. 7, the balloon 126 can be inflated and the distally located tissue perfused. The exiting perfusion liquid is shown by the arrows in FIG. 7. In particular, the perfusate liquid is pumped by pump 108 and associated conduit 122 through the hollow interior of the guide wire 124, so that it passes through the apertures or ports 140 in the support tube 136 to inflate the balloon 126 to the state shown in FIG. 7, while the remainder of that liquid flows out of the open distal end of the support tube 136, into the hollow interior of guide wire's tip 128, and out through the interface between the immediately adjacent convolutions of the tip. Accordingly, distally located tissue is oxygenated, notwithstanding the fact that the balloon is inflated and thus blocking the flow of blood through the bypass graft 10'.

The rate of flow of the infusate liquid is set by the flow control section switch and the ratio of that flow to the extraction flow rate is established by the ratio control switch of the flow control section. Accordingly, when ready the operator presses the foot pedal 114 to start the infusate pump. This action provides the infusate liquid through line 86 and through the associated components of the catheter 22', whereupon the infusate liquid exits from the catheter at the working tip 32' as described earlier. The rate of extraction of liquid through the annular space between the inner surface of the guide catheter 24 and the outer surface of the atherectomy catheter 22' is established by the extraction pump 90 under control of the associated flow controls of the console.

The turbine 70 is arranged to commence operation on a fixed time delay, e.g., 2 seconds, after the infusate pump commences operation in response to the depression of the foot pedal 114. This action causes the working head to begin rotating at a high rate of speed. The desired speed setting for the turbine is established by setting of the rotary knob of the speed control section of the console. Preferably some restraining means (not shown) is used to hold or clamp the guide wire in position when the atherectomy catheter is operated to prevent the rotation of the working head 32' from causing the guide wire to rotate. The compressed gas e.g., nitrogen or air, powering the turbine 70 of the atherectomy catheter 22' vents to the atmosphere via line 80. The debris particles produced by the rotary working head repeatedly impacting the plaque or other deposit within the diseased graft are withdrawn by the extraction pumps into the collection bag 92, in the same manner as discussed earlier. Any debris particles which may have otherwise escaped being withdrawn from the patient's body by the extraction subsystem are positively prevented from flowing distally by the barrier established by the inflated balloon 126. Thus, such particles will eventually be extracted. After the diseased bypass graft has been opened, the balloon 136 can be deflated by turning off the infusation pump. Then, the atherectomy catheter 22' and the guide wire 124 can be removed through the guide catheter 24.

It must be reiterated that the atherectomy catheter for producing the lumen through the vascular occlusion need not be a rotary impacting device, like described above. Thus, a system constructed in accordance with any embodiment of this invention may make use of any instrument having any type of working head, e.g., a reciprocating impacting working head, a combined rotary and reciprocating impacting working head, a rotary cutting head, a reciprocating cutting head, a rotary abrasive head, etc., to open the lumen in the occlusive material in the blood vessel. Moreover, the working head need not be shrouded. In fact, any of the heretofore identified prior art atherectomy devices can be utilized as part of the system 20 or 100. Some thrombectomy devices may also be utilized as part of the system 20 or 100. One such potential device is the Amplatz Thrombectomy Device designated by the trademark CLOT BUSTER by Microvena Corporation. It should also be pointed out that the working head of the device for forming the lumen need not even engage the occlusive material, so long as its lumen-opening operation produces debris particles to be removed. Thus, devices making use of liquidjets, laser beams, etc., can be utilized to open the lumen as part of the system of this invention. In short, any type of instrument for opening a lumen through the occlusive material and which produces debris can benefit from use in the system of this invention, i.e., a system which establishes a differential flow, wherein the infusate flow is less than the aspiration flow so that particles or pieces of occlusive material removed are positively precluded from flowing into adjacent vessels. Moreover, while the production of a local vortex flow adjacent the working head is desirable to effectuate the lumen opening process and to reduce debris particle size, it is not crucial to this invention.

Without further elaboration the foregoing will so fully illustrate my invention that others may, by applying current or future knowledge, adopt the same for use under various conditions of service.

What is claimed is:

1. An intravascular system for opening a lumen in a portion of an occluded blood vessel of a living being's vascular system, said occluded blood vessel portion being occluded by an occlusive material, said system comprising a lumen-opening member for introduction into the lumen of the blood vessel portion, debris blocking means, and debris extraction means, said lumen-opening member being arranged to act on the occlusive material in the interior of the occluded blood vessel portion to open the lumen for the freer flow of blood therethrough, whereupon some debris may be produced from the occlusive material by the action of said lumen-opening member, said debris blocking means being arranged to be located within the occluded blood vessel distally of said lumen opening member for preventing debris from flowing distally of said debris blocking means, said debris extraction means introducing an infusate liquid at a first flow rate adjacent said member and withdrawing said liquid at a second and higher flow rate to create a differential flow adjacent said lumen-opening member, whereupon debris produced by the action of said lumen-opening member is withdrawn by said differential flow for collection remote from the occluded vessel portion and is prevented from flowing into any upstream blood vessel or downstream blood vessel.

2. The intravascular system of claim 1 wherein the first and second flow rates are adjustable.

3. The intravascular system of claim 1 wherein said system comprises a catheter, said infusate liquid and the debris therein being withdrawn from the occluded blood vessel portion through said catheter.

4. The intravascular system of claim 1 wherein the first and second flow rates are correlated to each other.

5. The intravascular system of claim 4 wherein said first and second flow rates are adjustable.

6. The intravascular system of claim 1 wherein said lumen-opening member is tubular.

7. The intravascular system of claim 6 wherein said lumen-opening member comprises an elongated tubular instrument having distal end including a working head.

8. The intravascular system of claim 7 wherein said working head comprises a movable impacting member.

9. The intravascular system of claim 8 wherein said working head is rotatable.

10. A method for opening a lumen in a portion of an occluded blood vessel of a living being's vascular system, the occluded blood vessel portion being occluded by an occlusive material, said method comprising:

(a) providing a lumen-opening member into the lumen in the occluded blood vessel portion;

(b) providing debris extraction means within the being's vascular system adjacent said lumen-opening member;

(c) providing debris blocking means within the blood vessel-distally of said lumen opening member;

(d) causing said lumen-opening member to act on the occlusive material in the interior of the occluded blood vessel portion to open the lumen for the freer flow of blood therethrough, whereupon some debris may be produced from the occlusive material by the action of said member;

(e) causing said debris extraction means to introduce an infusate liquid at a first flow rate adjacent said member; and (f) causing said debris extraction means to withdraw said liquid at a second and higher flow rate to create a differential flow adjacent said member, whereupon debris produced by the operation of said member is withdrawn for collection remote from the occluded blood vessel portion and whereupon said debris blocking means blocks debris from flowing distally of said debris blocking means.

11. The method of claim 10 wherein said occluded blood vessel portion comprises a bypass graft.

12. The method of claim 11 wherein said bypass graft is a coronary bypass graft.

13. The method of claim 11 wherein said differential flow prevents debris produced by the action of said member from flowing into either the a first blood vessel portion or a second blood vessel portion.

14. The method of claim 13 wherein said occluded blood vessel portion comprises a bypass graft.

15. The method of claim 14 wherein said bypass graft is a coronary bypass graft and wherein said first vessel portion comprises the aorta.

16. The method of claim 14 wherein said occluded blood vessel portion comprises a portion of the femoral artery.

17. The method of claim 14 wherein said first blood vessel portion comprises the profunda femoris.

18. The method of claim 10 wherein said occluded blood vessel portion comprises a portion of an artery.

19. The method of claim 18 wherein said artery is a coronary artery.

20. The method of claim 18 wherein said artery is a femoral artery.

21. An intravascular system for opening a lumen in a portion of an occluded blood vessel of a living being's vascular system, said occluded blood vessel portion being occluded by an occlusive material, said system comprising a catheter, a lumen-opening member, and debris extraction means, said catheter having a longitudinal passageway extending at least partially therethrough, said lumen-opening member being arranged for introduction through said passageway into the lumen of the blood vessel portion to act on the occlusive material in the interior of the occluded blood vessel portion to open the lumen for the freer flow of blood therethrough, whereupon some debris may be produced from the occlusive material by the action of said lumen-opening member thereon, said debris extraction means introducing an infusate liquid at a first flow rate adjacent said lumen-opening member and withdrawing said liquid at a second and higher flow rate through said passageway of said catheter to create a differential flow adjacent said lumen-opening member, whereupon debris produced by the action of said lumen-opening member on the occlusive material is withdrawn by said differential flow through said passageway for collection remote from the occluded vessel portion and is prevented from flowing into any upstream blood vessel or downstream blood vessel.

22. The intravascular system of claim 21 wherein the first and second flow rates are adjustable.

23. The intravascular system of claim 21 wherein said system comprises a catheter, said infusate liquid and the debris therein being withdrawn from the occluded blood vessel portion through said catheter.

24. The intravascular system of claim 23 wherein the first and second flow rates are correlated to each other.

25. The intravascular system of claim 24 wherein said first and second flow rates are adjustable.

26. The intravascular system of claim 21 wherein said lumen-opening member is tubular.

27. The intravascular system of claim 26 wherein said lumen-opening member comprises an elongated tubular instrument having distal end including a working head.

28. The intravascular system of claim 27 wherein said working head comprises a movable impacting member.

29. The intravascular system of claim 28 wherein said working head is rotatable.

* * * * *

UNITED STATES PATENT AND TRADEMARK OFFICE
CERTIFICATE OF CORRECTION

PATENT NO. : 5,938,672  
DATED : August 17, 1999  
INVENTOR(S) : John E. Nash

Page 1 of 1

It is certified that error appears in the above-identified patent and that said Letters Patent is hereby corrected as shown below:

<u>Title Page,</u>  
Under the heading "Related U.S. Application Data":

Line 2, delete "abandoned" and insert -- Pat. No. 5,879,361 --.

Signed and Sealed this

Twenty-fifth Day of September, 2001

*Attest:*

NICHOLAS P. GODICI

*Attesting Officer*     *Acting Director of the United States Patent and Trademark Office*